(12) United States Patent
Heismann

(10) Patent No.: US 9,747,702 B2
(45) Date of Patent: Aug. 29, 2017

(54) METHOD AND APPARATUS FOR ACQUIRING A HIGH-RESOLUTION MAGNETIC RESONANCE IMAGE DATASET OF AT LEAST ONE LIMITED BODY REGION HAVING AT LEAST ONE ANATOMICAL STRUCTURE OF A PATIENT

(71) Applicant: Siemens Aktiengesellschaft, Munich (DE)

(72) Inventor: Bjoern Heismann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 62 days.

(21) Appl. No.: 14/865,108

(22) Filed: Sep. 25, 2015

(65) Prior Publication Data
US 2016/0093072 A1 Mar. 31, 2016

(30) Foreign Application Priority Data
Sep. 25, 2014 (DE) .......................... 10 2014 219 376

(51) Int. Cl.
*G06K 9/00* (2006.01)
*G06T 11/00* (2006.01)
(Continued)

(52) U.S. Cl.
CPC .......... *G06T 11/003* (2013.01); *A61B 5/0037* (2013.01); *A61B 5/055* (2013.01);
(Continued)

(58) Field of Classification Search
CPC ....... A61B 6/037; A61B 2576/00; A61B 6/03; A61B 5/055; A61B 2090/374;
(Continued)

(56) References Cited

U.S. PATENT DOCUMENTS 5,531,520 A * 7/1996 Grimson ................ G01B 11/25
382/131
5,818,231 A * 10/1998 Smith .................... G01R 33/58
324/307

(Continued)

OTHER PUBLICATIONS

Lambregts et al., "Accuracy of Gadofosveset-enhanced MRI for Nodal Staging and Restaging in Rectal Cancer," Annals of Surgery, vol. 253, Nr. 3, pp. 539-545 (2011).

*Primary Examiner* — Vu Le
*Assistant Examiner* — Aklilu Woldemariam
(74) *Attorney, Agent, or Firm* — Schiff Hardin LLP

(57) ABSTRACT

In a method and magnetic resonance apparatus for acquiring a high-resolution magnetic resonance image dataset of at least one limited body region having at least one anatomical structure of a patient, an overview image dataset is first acquired, using which an item of position information of the at least one anatomical structure is ascertained, the item of position information designating an exact position of the at least one anatomical structure and/or a relative position of the at least one anatomical structure relative to the reference body region. A high-resolution magnetic resonance image dataset of the anatomical structure is then created using the position information and the high-resolution magnetic resonance image dataset is evaluated. The evaluated high-resolution image data is then made available in electronic form.

7 Claims, 2 Drawing Sheets

(51) Int. Cl.
*A61B 5/055* (2006.01)
*A61B 5/00* (2006.01)
*G01R 33/56* (2006.01)
*G01R 33/563* (2006.01)
*G01R 33/54* (2006.01)

(52) U.S. Cl.
CPC .......... *A61B 5/418* (2013.01); *A61B 2576/00* (2013.01); *G01R 33/543* (2013.01); *G01R 33/5601* (2013.01); *G01R 33/56341* (2013.01); *G01R 33/56366* (2013.01); *G06K 9/00* (2013.01)

(58) Field of Classification Search
CPC .. A61B 2017/00039; A61B 2034/2065; A61B 5/4094; A61B 8/543; A61B 2090/3954; A61B 5/06; A61B 6/488; A61B 8/13; A61B 5/0555; A61B 2562/0223; A61B 5/103; A61B 6/5247; A61B 8/5215; A61B 8/5223; A61B 5/0037; A61B 5/418; G06T 2207/10072; G06T 2207/10088; G06T 2207/30004; G06T 7/0012; G06T 2207/10081; G06T 3/0068; G06T 7/11; G06T 2207/10104; G06T 11/003; G01R 33/481; G01R 33/56; G01R 33/58; G01R 33/4808; G01R 33/30; G01R 33/4814; G01R 33/54; G01R 33/56316; G01R 33/4826; G01R 33/4835; G01R 33/543; G01R 33/5601; G01R 33/56341; G01R 33/56366; Y02T 10/6286; Y10S 903/93; A61K 49/06; A61N 2005/1055; G05B 2219/45117; G06K 2209/057; G06K 9/6292; E21B 47/122
USPC ........ 382/128, 129, 130, 131, 132; 600/410, 600/414; 324/309, 307, 300, 310, 311, 324/312, 313
See application file for complete search history.

(56) References Cited

U.S. PATENT DOCUMENTS

| | | | | |
|---|---|---|---|---|
| 6,486,667 | B1* | 11/2002 | Wu | G01R 33/4828 324/306 |
| 6,529,762 | B1* | 3/2003 | Ladebeck | A61B 5/055 324/309 |
| 8,909,325 | B2* | 12/2014 | Kimchy | G01T 1/161 600/407 |
| 2002/0128550 | A1* | 9/2002 | Van Den Brink | A61B 8/00 600/411 |
| 2003/0208116 | A1* | 11/2003 | Liang | A61B 5/055 600/407 |
| 2006/0239529 | A1* | 10/2006 | Kuth | A61B 5/055 382/130 |
| 2007/0239009 | A1* | 10/2007 | Kawashima | A61B 8/12 600/437 |
| 2010/0166274 | A1* | 7/2010 | Busch | G06T 11/006 382/131 |
| 2010/0217110 | A1* | 8/2010 | Hughes | A61B 5/055 600/410 |
| 2012/0150048 | A1* | 6/2012 | Kang | A61B 6/508 600/481 |
| 2012/0165652 | A1* | 6/2012 | Dempsey | A61N 5/1045 600/411 |
| 2014/0055132 | A1* | 2/2014 | Biber | G01R 33/3664 324/307 |
| 2014/0193053 | A1* | 7/2014 | Kadoury | G06T 11/008 382/131 |
| 2015/0366527 | A1* | 12/2015 | Yu | A61B 5/055 382/131 |

* cited by examiner

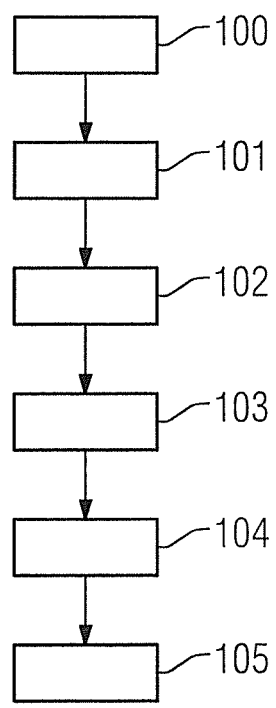

METHOD AND APPARATUS FOR ACQUIRING A HIGH-RESOLUTION MAGNETIC RESONANCE IMAGE DATASET OF AT LEAST ONE LIMITED BODY REGION HAVING AT LEAST ONE ANATOMICAL STRUCTURE OF A PATIENT

BACKGROUND OF THE INVENTION

Field of the Invention

The present invention concerns a method for acquiring a high-resolution magnetic resonance image dataset of at least one limited body region having at least one anatomical structure of a patient. The present invention also concerns a magnetic resonance apparatus, and a storage medium encoded with programming instructions that are designed to implements such a method.

Description of the Prior Art

The standard clinical primary diagnosis of lymph nodes is implemented by computed tomography. Lymph nodes having an effective diameter of 1 cm to 2 cm are categorized as healthy. Above a size of 3 cm, a pathological change is generally assumed. There is a diagnostic gray area in-between that presents great problems in the identification of treatment in clinical oncological practice as a consequence. A more specific analysis by means of magnetic resonance tomography is therefore very desirable.

SUMMARY OF THE INVENTION

An object of the present invention is to enable detailed analysis of individual body regions having an anatomical structure using a high-resolution image dataset.

This object is achieved in accordance with the invention by a method for acquiring a high-resolution magnetic resonance image dataset of at least one limited body region having at least one anatomical structure of a patient by operation of a magnetic resonance apparatus that includes the following steps.

An overview image dataset of the patient is acquired, the overview image dataset including image data of the at least one limited body region having the at least one anatomical structure, and at least one reference body region, which is located separately from the at least one limited body region inside the patient.

At least one item of position information of the at least one anatomical structure is determined using the overview image dataset, the at least one item of position information of the at least one anatomical structure including an exact position of the at least one anatomical structure inside the patient and/or a relative position of the at least one anatomical structure relative to the at least one reference body region.

A high-resolution magnetic resonance image dataset of the at least one limited body region is acquired, with a recording window of the high-resolution magnetic resonance image dataset being fixed using the at least one item of position information.

The high-resolution magnetic resonance image dataset is evaluated in the computer to produce evaluated high-resolution image data.

The evaluated high-resolution image data is made available as an electronic signal, such as a data file from the computer.

As used herein, a limited body region means a body region that includes a section of the patient that is medically significant for the pending magnetic resonance examination.

Furthermore, an anatomical structure as used herein means, for example, a self-contained anatomical structure of the patient which is separated from a region surrounding the anatomical structure, such as, for example, due to a different functionality and/or different types of tissue. The anatomical structure can include, for example, an organ or a section of an organ. The limited body region preferably includes a lymph node region of the patient, in particular a region within which a lymph node is situated, so the anatomical structure is formed by the lymph nodes within the limited body region. The reference region of the patient preferably is a further body region of the patient, with the reference region being taken into account during a medical inspection of the anatomical structure. The reference region can be, for example, a tumor region, so the effects thereof on the lymph nodes of the patient can be inspected.

A separate arrangement and/or formation of the at least one anatomical structure from the at least one reference region as used herein means that the anatomical structure and the reference region are situated at different spatial positions inside the patient and/or that the anatomical structure and the reference region have different functionalities inside the body of the patient.

Furthermore, an overview image dataset means an image dataset that has a large coverage area of the patient, such as by way of example the entire body of the patient. The choice of coverage area is preferably adapted to the reference region and the anatomical structure inside the patient. For example, the coverage area of the overview image dataset can also be just a thorax region or a head-neck-throat region, etc. of the patient with a corresponding choice of the reference region and/or anatomical structure. Preferably both the reference region and the at least one limited body region having the at least one anatomical structure can be detected from evaluated overview image data. The evaluated overview image data can be in the form of two-dimensional slice images or in the form of three-dimensional image data. A contrast medium can have been administered to the patient before the detection of the overview image dataset and/or the detection of the high-resolution magnetic resonance image dataset.

A resolution, in particular a spatial resolution, of the overview image dataset is preferably lower than a resolution, in particular a spatial resolution, of the high-resolution magnetic resonance image dataset. A resolution, in particular a spatial resolution, of the high-resolution magnetic resonance image dataset preferably is at least one pixel per millimeter of the at least one anatomical structure of the at least one limited body region. The evaluated high-resolution image data maps the at least one limited section having the at least one anatomical structure, so the anatomical structure can be displayed with an advantageously high resolution for the medical operating personnel, such as a physician.

The evaluated high-resolution image data can be depicted or displayed at a display screen, for example of a monitor, for a medical operator, in particular a physician. Alternatively or additionally, the evaluated high-resolution image data may be stored in a memory, so the evaluated high-resolution image data can be retrieved at any time by the medical operator, in particular a physician, for an analysis of the image data.

Individual body regions, which have an anatomical structure relevant to a medical examination and/or medical interrogation, for example lymph nodes of a patient, can advantageously firstly be exactly localized by the inventive method using the overview dataset. The individual body regions can then be obtained using position information, which is obtained from the overview dataset, so as to be displayed with high resolution for the medical examination and/or medical interrogation and be subjected to closer inspection and/or analysis in this way by the medical operator, in particular a physician. Anatomical abnormalities in the anatomical structure can be seen in the high-resolution image data that cannot be seen in the overview image dataset.

In a further embodiment of the invention, the at least one anatomical structure of the at least one limited body region is measured using the evaluated high-resolution image data. Measuring in this connection means the determination of a size of the at least one anatomical structure. A patient-specific and/or anatomical abnormality of the at least one anatomical structure can be easily acquired in this way and provided to a medical operator for further analysis. If, for example, the at least one anatomical structure is a lymph node, the size of the lymph node can be easily and quickly determined in this way. Using the size of a lymph node a physician can draw a conclusion about the health of the lymph node.

Also in accordance with the invention, the evaluation of the high-resolution magnetic resonance image dataset includes the determination of at least one functional parameter of the at least one anatomical structure of the at least one limited body region. A medical operator thus can be provided with further parameters for detailed and/or specific medical analysis and/or diagnosis. Furthermore, the significance of a diagnosis and/or analysis can advantageously be increased by the functional parameters. The functional parameters are preferably supplied to the medical operator, in particular a physician, together with the evaluated high-resolution image data. The functional parameters can include a diffusivity and/or a contrast medium perfusion and/or magnetic resonance-spectroscopic data. Determination of further parameters and/or functional parameters that are considered expedient to those skilled in the art are also suitable.

In a further embodiment of the invention, at least one correlation parameter is calculated using the at least one item of position information for the at least one anatomical structure of the at least one limited body region. The correlation parameter designates a correlation of the at least one anatomical structure with respect to the reference region. A possible correlation and/or impact and/or effect of the reference region on the at least one anatomical structure can be acquired in this connection. If, for example, the reference region includes a tumor region, a possible effect by the tumor of the tumor region on individual lymph nodes of the patient can be acquired and/or ascertained. A further formation of the reference region is also possible at any time.

The at least one correlation parameter also can designate a distance between the at least one anatomical structure and the reference region and/or a probability of metastases. A medical operator, in particular a physician, can be supplied with additional information for a medical analysis hereby. In the example of a depiction of multiple anatomical structures, by these correlation parameters assist, a physician in making an assessment of the individual anatomical structures and/or the physician can use these correlation parameters as a sorting criterion for the multiple anatomical structures. In this context, the anatomical structures are each formed by a lymph node of the patient, and these are sorted, for example, using their distance from a tumor. The determination of the probability of metastases for individual anatomical structures includes a distance of the respective anatomical structure from the reference region.

A particularly high resolution, such as spatial resolution, of the acquired image data can be achieved when the acquired image data of the high-resolution magnetic resonance image dataset has a resolution of at least one pixel per millimeter of the at least one anatomical structure of the at least one limited body region. A particularly detailed analysis of the at least one anatomical structure can be enhanced and/or enabled in this way for a physician using the supplied image data of the high-resolution magnetic resonance image dataset. A separate high-resolution magnetic resonance image dataset for each anatomical structure can be made available here for an evaluation.

The present invention also encompasses a magnetic resonance apparatus having a scanner, a system control computer and a user interface, wherein the system control unit includes a correlation processing hardware or software and evaluation processing hardware or software that are designed to implement the method for acquiring a high-resolution magnetic resonance image dataset of at least one limited body region having at least one anatomical structure of a patient, as described above.

The scanner is operated to acquire an overview image dataset of the patient, wherein the overview image dataset includes image data of the at least one limited body region having the at least one anatomical structure and at least one reference body region, which is located separately from the at least one limited body region inside the patient.

The control computer is configured to determine at least one item of position information of the at least one anatomical structure using the overview image dataset, wherein the at least one item of position information of the at least one anatomical structure comprises an exact position of the at least one anatomical structure inside the patient and/or a relative position of the at least one anatomical structure relative to the at least one reference body region.

The scanner is operated to acquire a high-resolution magnetic resonance image dataset of the at least one limited body region, with a recording window of the high-resolution magnetic resonance image dataset being fixed using the at least one item of position information.

The control computer is configured to evaluate the high-resolution magnetic resonance image dataset so as to produce evaluated high-resolution image data, and to supply evaluated high-resolution image data as an electronic signal, such as a data file, from the control computer.

Individual body regions, which have an anatomical structure relevant to a medical examination and/or medical interrogation, such as lymph nodes of a patient, can thus be first exactly localized by the overview dataset. Using position information, which is obtained from the overview dataset, the individual body regions can then be displayed in high resolution for the medical examination and/or medical interrogation and in this way be subjected by the medical operator, in particular a physician, to closer inspection and/or analysis. In particular anatomical abnormalities in the anatomical structure can be seen in the high-resolution image data that cannot be seen in the overview image dataset.

The advantages of the inventive magnetic resonance device substantially correspond to the advantages of the inventive method for acquiring a high-resolution magnetic resonance image dataset of at least one limited body region having at least one anatomical structure of a patient.

The invention also encompasses a non-transitory, computer-readable data storage medium that can be loaded directly into a memory of programmable system control computer of a magnetic resonance apparatus. The storage medium is encoded with programming instructions that cause the control computer to implement the method for acquiring a high-resolution magnetic resonance image dataset of at least one limited body region having at least one anatomical structure of a patient, when the programming instructions are executed in the system control computer of the magnetic resonance device.

BRIEF DESCRIPTION OF THE DRAWINGS

FIG. 2 is a flowchart of the inventive method for acquiring a high-resolution magnetic resonance image dataset of at least one limited body region having at least one anatomical structure of a patient.

DESCRIPTION OF THE PREFERRED EMBODIMENTS

Figure 1:
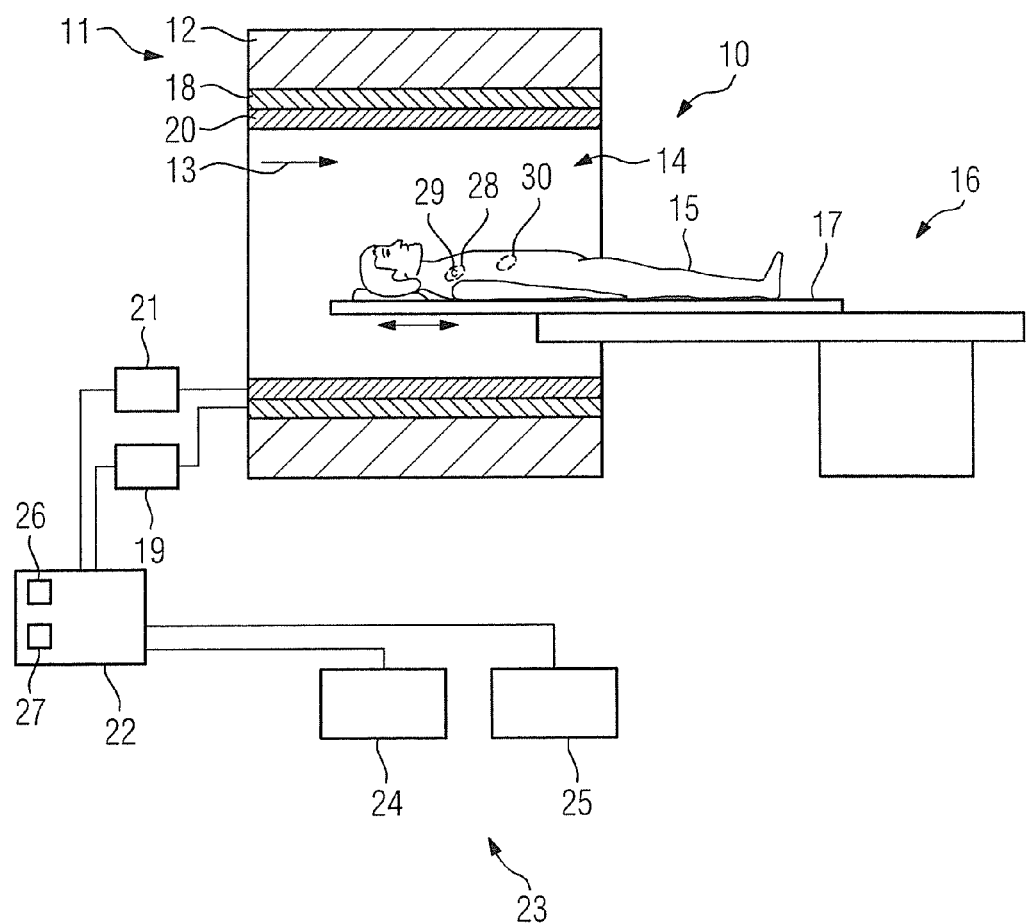
FIG. 1 schematically illustrates an inventive magnetic resonance apparatus.

FIG. 1 schematically shows a magnetic resonance apparatus 10. The magnetic resonance apparatus 10 has a scanner 11 that includes a superconductive basic field magnet 12 for generating a strong and constant basic magnetic field 13. The scanner 11 has a patient-receiving region 14 for receiving a patient 15. In the present exemplary embodiment the patient-receiving region 14 is cylindrical and cylindrically surrounded in a circumferential direction by the basic field magnet 12. A design of the patient-receiving region 14 that differs from this is possible. The patient 15 can be moved by a patient-positioning device 16 of the magnetic resonance apparatus 10 into the patient-receiving region 14. The patient-positioning device 16 has an examination table 17 designed so as to move inside the patient-receiving region 14.

The scanner 11 also has a gradient coil unit 18 for generating magnetic field gradients that are used for spatial encoding during imaging. The gradient coil unit 18 is controlled by a gradient control unit 19 of the magnetic resonance apparatus 10. The scanner 11 also has a radio-frequency antenna unit 20, which in the present exemplary embodiment is designed as a body coil permanently integrated in the scanner 11. The radio-frequency antenna unit 20 is designed to excite nuclear spins in the patient 15 so as to be deflected from the polarization that is established in the basic magnetic field 13 generated by the basic field magnet 12. The radio-frequency antenna unit 20 is controlled by a radio-frequency antenna control unit 21 of the magnetic resonance apparatus 10 and radiates radio-frequency magnetic resonance sequences into an examination volume that is formed substantially by the patient-receiving region 14 of the scanner 11. The radio-frequency antenna unit 20 is also designed to receive magnetic resonance signals.

The magnetic resonance apparatus 10 has a system control computer 22 to control the basic field magnet 12, the gradient control unit 19 and to control the radio-frequency antenna control unit 21. The system control computer 22 centrally controls the magnetic resonance apparatus 10, in particular the scanner 11 thereof, to execute a predetermined imaging gradient echo sequence for example. The system control computer 22 also has an evaluation processor 26 for evaluation of medical image data that are acquired during the magnetic resonance examination. The magnetic resonance apparatus 10 also has a user interface 23 that is connected to the system control computer 22. Control information, for example imaging parameters, and reconstructed magnetic resonance images can be displayed on a display unit 24, for example at least one monitor, of the user interface 23 for a medical operator. The user interface 23 also has an input unit 25 via which information and/or parameters can be entered by the medical operator during a measuring process.

In the exemplary embodiment the system control computer 22 also has a correlation processor 27. The system control computer 22, the correlation processor 27 and the evaluation processor 26, together with the scanner 11, are configured to implement an inventive method for acquiring a high-resolution magnetic resonance image dataset of at least one limited body region 28 having at least one anatomical structure 29 of a patient 15. For this purpose, the system control computer 22 has appropriate software and/or computer programs that can be loaded into a memory of the system control computer 22, encoded with programming instructions that implement the method for acquiring a high-resolution magnetic resonance image dataset of at least one limited body region 28 having at least one anatomical structure 29 of a patient 15, when executed in the system control computer 22.

FIG. 2 is a flowchart of the method for acquiring a high-resolution magnetic resonance image dataset of at least one limited body region 28 having at least one anatomical structure 29 of the patient 15. In the method, individual body regions, which have an anatomical structure 29 relevant to a medical examination and/or medical interrogation, are first exactly localized with the use of an overview dataset, and then displayed in high-resolution using position information, which is obtained from the overview dataset, for the medical examination and/or medical interrogation.

In the exemplary embodiment, the method is illustrated using the example of a single limited body region 28 of the patient 15 which is formed by a lymph node region. The lymph node region includes a lymph node and a region around the lymph node. The single limited body region 28 includes the anatomical structure 29 that includes the lymph node of the patient 15. A reference region 30 of the patient 15 also includes a tumor region of the patient 15. In an alternative embodiment of the invention, the anatomical structure 29 and/or the reference region 30 can include further regions of a patient 15. It is also conceivable for more than one anatomical structure 29 to be displayed in the acquired image data and/or more than a single reference region 30 to be available for the inventive method.

First, for preparation, the patient 15 is positioned on the examination table 17 and introduced into the patient-receiving region 14. Then in a first method step 100 of the method, an overview image dataset of the patient 15 is acquired by operation of the scanner 11 by the system control computer 22. The overview image dataset includes image data of the limited body region 28, in particular of the lymph node region, having the anatomical structure 29, in particular having the lymph node. The overview image dataset image data also includes the reference region 30, in particular the tumor region, of the patient 15. The tumor region and lymph node region are, moreover, localized and/or arranged separately from each other inside the patient 15. Depending on the choice of lymph node region of the patient 15 and a position of the tumor region inside the patient 15 the overview image dataset comprises by way of example a thorax region of the patient 15, an abdomen region of the patient 15, a head-throat-neck region of the patient 15 or further body regions of the patient 15 that are considered expedient to those skilled in the art.

In a subsequent method step 101, the acquired overview image dataset is evaluated by means of the system control computer 22, in particular the evaluation unit 26. In method step 101 image data are created that include both the reference region 30 and the limited body region 28 of the patient 15. If required or possible, a detail of the image data may also be focused on in method step 101, wherein the detail of the image data comprises both the reference region 30 and the limited body region 28 of the patient 15. The evaluated image data can include two-dimensional slice images or three-dimensional volume data.

In a further method step 102, at least one item of position information of the anatomical structure 29, in particular of the lymph node, is determined by the evaluation processor 26 of the system control computer 22, using the evaluated image data. The position information can include an exact position of the lymph node inside the patient 15 or a relative position of the lymph node based on the tumor region of the patient 15. The determination of the position of the lymph node includes both the position information of the overview image dataset and an anatomical position of the lymph node inside the patient 15 that is known per se. The anatomical position of the lymph node inside the patient 15 that is known per se can be stored in a database and be retrieved for determining the position information. Alternatively or additionally, the anatomical position of the lymph node inside the patient 15 that is known can also be manually communicated by a medical operator, in particular a physician, via the user interface 23 of the system control computer 22, in particular the evaluation processor 26. The anatomical position of the lymph node inside the patient 15 that is known is substantially the same for all patients 15. An exact, patient-specific position of the lymph node is only ascertained and/or determined in method step 102 of the determination of the at least one item of position information with the use of the overview image dataset.

Furthermore, at least one correlation parameter for the anatomical structure 29, in particular the lymph node, of the patient 15 is calculated in this method step 102 by the correlation processor 27 of the system control computer 22. The correlation parameter includes a correlation of the lymph node in relation to the reference region 30, in particular the tumor region, of the patient 15. The correlation parameter can be, for example, a distance of the lymph node from the tumor region of the patient 15. Alternatively or additionally, the correlation parameter can include a probability of metastases for the lymph node, wherein the probability of the metastases for the corresponding lymph node is ascertained by the correlation processor 27 using the distance of the lymph node from the tumor region. The probability of metastases for the chosen lymph node is automatically determined by the correlation processor 27.

If, for example, two or more lymph nodes are displayed inside the overview image dataset, the position information and/or the correlation information is ascertained for each individual lymph node in the further method step 102 by the evaluation processor 26 together with the correlation processor 27. Using the position information and/or the correlation information a sorting of the individual lymph nodes can be created, moreover, in the further method step 102 by the evaluation processor 26 and/or correlation processor 27, wherein sorting occurs using the position information or the correlation parameter. A selection criterion, according to which position information or according to which correlation parameter the sorting should occur, can be entered by the medical operator via the user interface 23. The results of the sorting can be communicated and/or provided as an output to the medical operator, for example a physician, in a list at the user interface 23.

In a further method step 103, a high-resolution magnetic resonance image dataset is acquired by operation of the scanner 11 and by the system control computer 22. The high-resolution magnetic resonance image dataset includes the lymph node region of the patient 15, with a recording window of the high-resolution magnetic resonance image dataset being fixed using the at least one item of position information determined in the further method step 102.

A resolution, in particular a spatial resolution, of the high-resolution magnetic resonance image dataset is greater than a resolution of the overview image dataset. The image data of the high-resolution magnetic resonance image dataset include a resolution, in particular a spatial resolution, of at least one pixel per millimeter of the anatomical structure 29, in particular of the lymph node. Furthermore, it is also conceivable in an alternative embodiment for the image data of the high-resolution magnetic resonance image dataset to have a much higher resolution, in particular spatial resolution. For example, a resolution, in particular a spatial resolution, of the image data of the high-resolution magnetic resonance image dataset can be at least one pixel per 0.5 millimeter of the anatomical structure 29, in particular of the lymph node. The high-resolution magnetic resonance image dataset can include both two-dimensional slice images and three-dimensional volume data. Alternatively or additionally, an acquisition of the high-resolution magnetic resonance image dataset is also possible in which the high-resolution magnetic resonance image data is focused on the chosen lymph node, for example due to a partial excitation of a chosen imaging volume and/or by an excitation using specific gradient sequences.

In a further method step 104, the high-resolution magnetic resonance image dataset is evaluated by the evaluation processor 26 of the system control computer 22 and evaluated high-resolution image data are thus determined. Using the evaluated high-resolution image data the anatomical structure 29, in the present exemplary embodiment the lymph nodes, is measured by the evaluation unit 26 in the further method step 204. A size, in particular an absolute size, of the lymph node is preferably determined here by the evaluation unit 26.

The evaluation of the high-resolution magnetic resonance image dataset in the further method step 104 also includes a determination of at least one functional parameter of the lymph node, wherein the functional parameter is likewise determined by the evaluation unit 26. The functional parameter can include a diffusivity and/or a contrast medium perfusion and/or magnetic resonance-specific data. Alternatively or additionally, the functional parameter can include further parameters that are considered expedient to those skilled in the art.

In order to determine the functional parameters formed by the contrast medium perfusion, a contrast medium is administered to the patient 15 before the acquisition of the high-resolution magnetic resonance image dataset and/or before the acquisition of the overview image dataset. Alternatively, high-resolution magnetic resonance image data of the lymph node and/or further anatomical structures 29 which were acquired without prior administration of contrast medium are also conceivable for this purpose.

In a further method step 105, the evaluated high-resolution image data are supplied by the system control computer 22. Supplying the evaluated high-resolution image data can include supplying the position information associated with the evaluated high-resolution image data and/or supplying the correlation parameters associated with the evaluated high-resolution image data and/or supplying the functional parameters associated with the evaluated high-resolution image data and/or supplying the size of the anatomical structure 29 associated with the evaluated high-resolution image data.

Supplying can include storing the evaluated high-resolution image data or the evaluated high-resolution image data together with the position information and/or the correlation parameters and/or the functional parameters and/or the size of the anatomical structure 29. Alternatively or additionally, supplying the evaluated high-resolution image data or the evaluated high-resolution image data together with the position information and/or the correlation parameters and/or the functional parameters and/or the size of the anatomical structure 29 can also include an output via the user interface 29 to the medical operator.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for evaluating metastases risk for anatomy in a patient, comprising:
    operating a magnetic resonance (MR) scanner, while a patient is situated therein, to acquire an overview image dataset, with an overview resolution, from only a limited body region of the patient that comprises less than an entirety of the patient, said overview image dataset representing a tumor in said limited body region and an anatomical structure, separate from said tumor in said body region, that is at risk of metastization by said tumor;
    providing said overview image dataset to a computer and, in said computer, determining position information from said overview image dataset that designates a relative position of said anatomical structure with respect to said tumor;
    in said computer, determining an operating sequence for said MR scanner, in which operating sequence an acquisition window is set dependent on said position information in order to obtain a high-resolution image dataset of said anatomical structure, said high-resolution image dataset being at a higher resolution than said overview resolution;
    operating said MR scanner to execute said operating sequence in order to obtain said high-resolution image dataset of said anatomical structure, said high-resolution magnetic resonance image dataset being comprised of a plurality of pixels, with said high-resolution magnetic resonance image dataset having a high-resolution of at least one pixel per millimeter of said anatomical structure in said limited body region;
    providing said high-resolution image dataset of said anatomical structure to said computer and, in said computer, calculating a correlation parameter, from said high-resolution image dataset and said position information, that designates a probability that said anatomical structure has metastasized due to said tumor; and
    in said computer, generating an electrical signal that represents the calculated correlation parameter, and making the electrical signal available as an output from said computer.

2. A method as claimed in claim 1 comprising, in said computer, additionally evaluating said high-resolution magnetic resonance image dataset by determining at least one functional parameter of said anatomical structure in said limited body region.

3. A method as claimed in claim 2 comprising selecting said at least functional parameter from the group consisting of diffusivity, contrast medium perfusion, and magnetic resonance spectroscopic data.

4. A method as claimed in claim 1 comprising calculating said correlation parameter dependent on a distance between said anatomical structure and said tumor.

5. A method as claimed in claim 1 wherein said anatomical structure is a lymph node.

6. A magnetic resonance (MR) apparatus comprising:
    an MR scanner;
    a computer configured to operate said MR scanner, while a patient is situated therein, to acquire an overview image dataset, with an overview resolution, from only a limited body region of the patient that comprises less than an entirety of the patient, said overview image dataset representing a tumor in said limited body region and an anatomical structure, separate from said tumor in said body region, that is at risk of metastization by said tumor;
    said computer being configured to determine position information from said overview image dataset that designates a relative position of said anatomical structure with respect to said tumor;
    said computer being configured to determine an operating sequence for said MR scanner, in which operating sequence an acquisition window is set dependent on said position information in order to obtain a high-resolution image dataset of said anatomical structure, said high-resolution image dataset being at a higher resolution than said overview resolution;
    said computer being configured to operate said MR scanner to execute said operating sequence in order to obtain said high-resolution image dataset of said anatomical structure, said high-resolution magnetic resonance image dataset being comprised of a plurality of pixels, with said high-resolution magnetic resonance image dataset having a high-resolution of at least one pixel per millimeter of said anatomical structure in said limited body region;
    said computer being configured to calculate a correlation parameter, from said high-resolution image dataset and said position information, that designates a probability that said anatomical structure has metastasized due to said tumor; and
    said computer being configured to generate an electrical signal that represents the calculated correlation parameter, and to make the electrical signal available as an output from said computer.

7. A non-transitory, computer-readable data storage medium encoded with programming instructions, said storage medium being loaded into a computer of a magnetic resonance (MR) apparatus that comprises an MR scanner, said programming instructions causing said computer to:
    operate said MR scanner, while a patient is situated therein, to acquire an overview image dataset, with an overview resolution, from only a limited body region of the patient that comprises less than an entirety of the patient, said overview image dataset representing a tumor in said limited body region and an anatomical structure, separate from said tumor in said body region, that is at risk of metastization by said tumor;

determine position information from said overview image dataset that designates a relative position of said anatomical structure with respect to said tumor;

determine an operating sequence for said MR scanner, in which operating sequence an acquisition window is set dependent on said position information in order to obtain a high-resolution image dataset of said anatomical structure, said high-resolution image dataset being at a higher resolution than said overview resolution;

operate said MR scanner to execute said operating sequence in order to obtain said high-resolution image dataset of said anatomical structure, said high-resolution magnetic resonance image dataset being comprised of a plurality of pixels, with said high-resolution magnetic resonance image dataset having a high-resolution of at least one pixel per millimeter of said anatomical structure in said limited body region;

calculate a correlation parameter, from said high-resolution image dataset and said position information, that designates a probability that said anatomical structure has metastasized due to said tumor; and generate an electrical signal that represents the calculated correlation parameter, and make the electrical signal available as an output from said computer.

* * * * *